US011668211B2

(12) United States Patent
Mauthofer et al.

(10) Patent No.: US 11,668,211 B2
(45) Date of Patent: Jun. 6, 2023

(54) PRESSURE MEASURING UNIT AND CONNECTION UNIT FOR A MOTOR VEHICLE TRANSMISSION

(71) Applicant: Vitesco Technologies Germany GMBH, Hannover (DE)

(72) Inventors: Thomas Mauthofer, Nuremberg (DE); Gerhard Bullinger, Burgoberbach (DE)

(73) Assignee: Vitesco Technologies GmbH, Hannover (DE)

( * ) Notice: Subject to any disclaimer, the term of this patent is extended or adjusted under 35 U.S.C. 154(b) by 344 days.

(21) Appl. No.: 16/902,704

(22) Filed: Jun. 16, 2020

(65) Prior Publication Data
US 2020/0378282 A1 Dec. 3, 2020

Related U.S. Application Data

(63) Continuation of application No. PCT/EP2018/084489, filed on Dec. 12, 2018.

(30) Foreign Application Priority Data

Dec. 19, 2017 (DE) ...................... 10 2017 223 177.7

(51) Int. Cl.
*F01M 1/20* (2006.01)
*G01N 33/28* (2006.01)

(52) U.S. Cl.
CPC ........... *F01M 1/20* (2013.01); *G01N 33/2888* (2013.01)

(58) Field of Classification Search
CPC ... F01M 1/00; F01M 1/18; F01M 1/20; F16H 61/00; F16H 61/0003; F16H 61/0006;
(Continued)

(56) References Cited

U.S. PATENT DOCUMENTS 7,737,701 B2 * 6/2010 Williamson ....... G01R 31/2812
324/538
8,261,618 B2   9/2012 Engle et al.
(Continued)

FOREIGN PATENT DOCUMENTS

CN   103314284 A   9/2013
CN   204314002 U   5/2015
(Continued)

OTHER PUBLICATIONS

Chinese Office Action dated Apr. 26, 2021 for corresponding Chinese Patent Application No. 201880076690.5.
(Continued)

*Primary Examiner* — Hoai-An D. Nguyen

(57) ABSTRACT

The example embodiment relates to a pressure measuring unit for determining the oil pressure in a motor vehicle transmission, including a circuit carrier, a pressure sensor, an electrical interface, a mechanical interface and a hydraulic interface. The pressure sensor is electrically connected to the circuit carrier by means of the electrical interface and mechanically connected to the circuit carrier by means of the mechanical interface on the first side of the circuit carrier. The hydraulic interface connecting the pressure measuring unit to a user hydraulic component is arranged on a side of the circuit carrier that is situated opposite the first side, and wherein an opening is arranged in the circuit carrier for pressure equalization between the pressure sensor and the hydraulic interface.

9 Claims, 2 Drawing Sheets

(58) Field of Classification Search
CPC ........ F16H 59/00; F16H 59/68; F16H 59/683; G01N 33/00; G01N 33/26; G01N 33/28; G01N 33/2888; G01L 19/00; G01L 19/0007; G01L 19/14; G01L 19/148
USPC .......... 324/378, 400, 401, 500, 537, 754.01, 324/754.03, 754.12, 754.15, 459, 460; 340/425.5, 438, 451, 500, 540, 603, 606, 340/611, 612, 614, 626
See application file for complete search history.

(56) References Cited

U.S. PATENT DOCUMENTS

| | | | |
|---|---|---|---|
| 2001/0011478 | A1 | 8/2001 | Fritzsche et al. |
| 2004/0118466 | A1 | 6/2004 | Ford et al. |
| 2004/0163477 | A1 | 8/2004 | Takashi et al. |
| 2005/0109156 | A1 | 5/2005 | Hellinger et al. |
| 2007/0169559 | A1 | 7/2007 | Hirosi |
| 2013/0032905 | A1 | 2/2013 | Lo et al. |

FOREIGN PATENT DOCUMENTS

| | | |
|---|---|---|
| DE | 19830538 A1 | 1/2000 |
| DE | 19834212 A1 | 1/2000 |
| DE | 102007003446 A1 | 8/2007 |
| DE | 102007052364 A1 | 5/2009 |
| EP | 1437532 A2 | 7/2004 |
| EP | 1533189 A2 | 5/2005 |
| JP | 2002521637 A | 7/2002 |
| JP | 2004197947 A | 7/2004 |
| JP | 2004219402 A | 8/2004 |
| JP | 2007192773 A | 8/2007 |
| JP | 3136087 U | 10/2007 |
| JP | 2015222175 A | 12/2015 |
| WO | WO-0003219 A2 * | 1/2000 ......... F16H 61/0006 |

OTHER PUBLICATIONS

Japenese Office Action dated Jun. 23, 2021 for corresponding Patent Application No. 2020-533589.
Korean Office Action dated Oct. 28, 2021 for corresponding Patent Application No. 10-2020-7020618.
Japanese Notice of Allowance dated Oct. 12, 2021 for corresponding Japanese Patent Application No. 2020-533589.
International Search Report and Written Opinion dated Mar. 25, 2019 from corresponding International Patent Application No. PCT/EP2018/084489.
German Office Action dated Aug. 17, 2018 for corresponding German Patent Application No. 10 2017 223 177.7.

* cited by examiner

PRESSURE MEASURING UNIT AND CONNECTION UNIT FOR A MOTOR VEHICLE TRANSMISSION

CROSS REFERENCE TO RELATED APPLICATIONS

This application claims the benefit of PCT Application PCT/EP2018/084489, filed Dec. 12, 2018, which claims priority to German Application DE 10 2017 223 177.7, filed Dec. 19, 2017. The disclosures of the above applications are incorporated herein by reference.

FIELD OF INVENTION

The invention relates to a pressure measuring unit and to a connection unit for transmission oil pressure sensors with electrical, mechanical and hydraulic interfaces.

BACKGROUND

In order to achieve low fuel consumption with low emissions, precise pressure data has to be recorded in motor vehicles. Various control processes of the motor vehicle can be influenced with this data.

Automatic transmissions for passenger cars are predominantly electronically controlled, wherein the electronic controller receives and evaluates the signals from several sensors in the motor vehicle. To this end, the pressure in the hydraulic oil of the transmission has to be measured with one or more sensors. Furthermore, modern engine controllers evaluate the intake vacuum and, to this end, require a pressure sensor which is accommodated in the intake tract.

The invention is provided for monitoring the oil pressure in motor vehicle transmissions. Furthermore, the invention is also suitable for use on automotive pressure sensors with increased media resistance requirements, e.g. for brake fluid, fuel, oils, urea and polluted air. Further areas of application are integrated or attached control devices in which hydraulic pressures have to be measured with pressure sensors.

For the purpose of coupling oil pressure sensors to an evaluation and/or control unit for transmissions, in particular for vehicle transmissions, arrangements are used which have separate interfaces for electrical power supply and signal transmission, for mechanical fastening of the pressure sensors and for connection to the hydraulic component to be monitored.

For the purpose of implementing the three interfaces, relatively large and complex housings are arranged around the pressure sensor. This entails high costs and large dimensions. In addition, the design of the housing is linked to the respective installation conditions, and therefore the electrical and mechanical interface has to be adapted by means of costly structures.

DE 198 34 212 A1 discloses a control device comprising a control circuit and a pressure sensor for measuring the hydraulic pressure in a transmission, which control circuit and pressure sensor are accommodated in a housing. The housing has a metal base plate which is connected to a hydraulic unit of the transmission in a pressure-tight manner. Said base plate is provided with a hole through which the pressure sensor is pressurized. A carrier for the pressure sensor has a cylindrical projection which is pressed into the hole in such a way that a pressure-tight and non-positive connection between the carrier and the base plate results due to material displacement. The arrangement requires a high level of manufacture outlay.

SUMMARY

The invention is based on providing a pressure measuring unit and a connection unit of the kind mentioned at the outset which allow a cost-effective and simple connection option.

The pressure measuring unit has a circuit carrier, a pressure sensor, an electrical, a mechanical and a hydraulic interface.

According to the example embodiment, the pressure sensor is electrically connected to the circuit carrier by means of the electrical interface and mechanically connected to the circuit carrier by means of the separate mechanical interface on the first side of the circuit carrier.

The hydraulic interface for connecting the pressure measuring unit to a user hydraulic component is arranged on a side of the circuit carrier that is situated opposite the first side, wherein an opening is arranged in the circuit carrier for pressure equalization between the pressure sensor and the hydraulic interface.

In this case, the hydraulic interface is detached from the pressure sensor, and the electrical and the mechanical interface are integrated in a pressure measuring unit and may be connected to a control unit in a cost-effective manner.

In addition, the pressure sensor is no longer in direct contact with the user interface, thus enabling a flexible installation position.

The electrical interface advantageously includes an electrical connecting part of the pressure sensor, for example a leadframe, and a contact area of the circuit carrier, for example a solder pad.

Furthermore, it is advantageous for the mechanical interface between the pressure sensor and the circuit carrier to be embodied by means of an adhesive bond. This standard procedure is widespread and cost-effective to implement.

The pressure sensor is embodied, in particular, as a surface-mountable SMD component. This enables a cost-effective design with high measurement accuracy together with a small size.

Furthermore, it is advantageous to embody the circuit carrier as a constituent part of a transmission control unit, as a result of which a particularly cost-effective embodiment is rendered possible.

In the connection unit according to the example embodiment, a user hydraulic component is connected to the pressure measuring unit by means of the hydraulic interface.

An advantageous refinement makes provision for the hydraulic connection to be connected to the user hydraulic component in a gas- or liquid-tight manner with respect to the surroundings by means of an annular sealing part. For example, a seal with an O-ring may be used for this purpose.

The hydraulic interface, which seals off the high-pressure environment, may therefore be implemented around the sensor unit independently of the sensor.

Miniaturization and simplification of the technique for connecting components of a user hydraulics system to a pressure sensor are achieved with this connection unit.

BRIEF DESCRIPTION OF THE DRAWINGS

The invention is explained in more detail below with reference to an example embodiment. In the associated drawings

DETAILED DESCRIPTION

Figure 1:
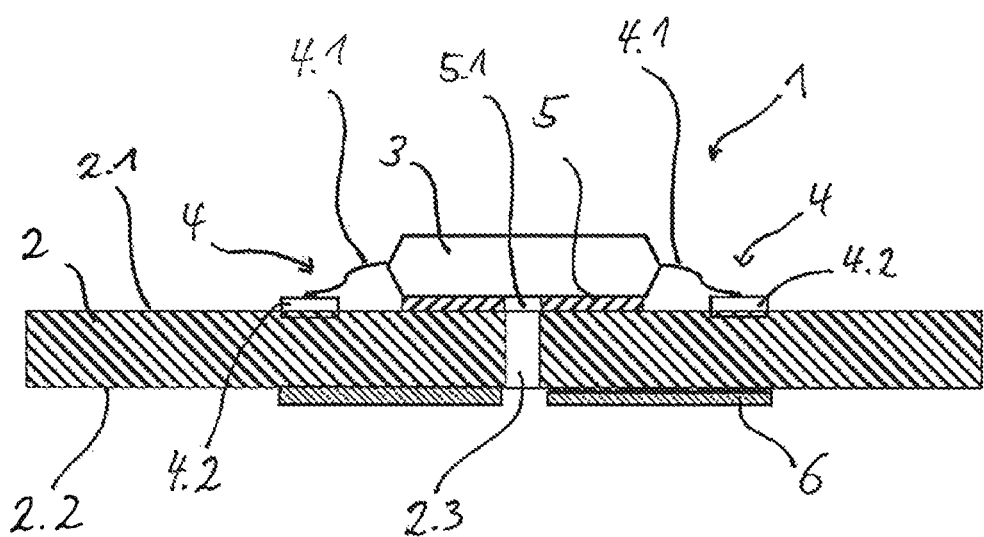
FIG. 1 shows a schematic illustration of the 1. pressure measuring unit.

FIG. 1 shows a pressure measuring unit 1 including a circuit carrier 2 and including a pressure sensor 3. The pressure measuring unit 1 also has an electrical, a mechanical and a hydraulic interface.

The pressure sensor 3 is electrically connected to the circuit carrier 2 by means of the electrical interface 4 and mechanically connected to the circuit carrier 2 by means of the mechanical interface 5 on the first side 2.1 of the circuit carrier 2, here the top side. A pressure sensor which is embodied as an SMD component is used as the pressure sensor 3.

Here, the electrical interface 4 has an electrical connecting part 4.1 of the pressure sensor 3, for example a leadframe, and a contact area 4.2 of the circuit carrier, for example a solder pad. For the sake of simplicity, the mechanical interface 5 is embodied by means of an adhesive bond here. For example, a standard epoxy resin may be used as the adhesive.

The hydraulic interface 6 for connecting the pressure measuring unit 1 to a user hydraulic component is arranged on the side 2.2 of the circuit carrier 2 that is situated opposite the first side 2.1, here the bottom side.

The hydraulic interface 6 may be implemented, for example, by the circuit carrier 2 or else by an additional component.

An opening 2.3 is arranged in the circuit carrier 2 in order to enable pressure equalization between the pressure sensor 3 on the top side of the circuit carrier 2 and the hydraulic interface 6 on the bottom side of the circuit carrier 2. To this end, the adhesive bond 5 between the pressure sensor 3 and the circuit carrier 2 has a corresponding opening 5.1.

Figure 2:
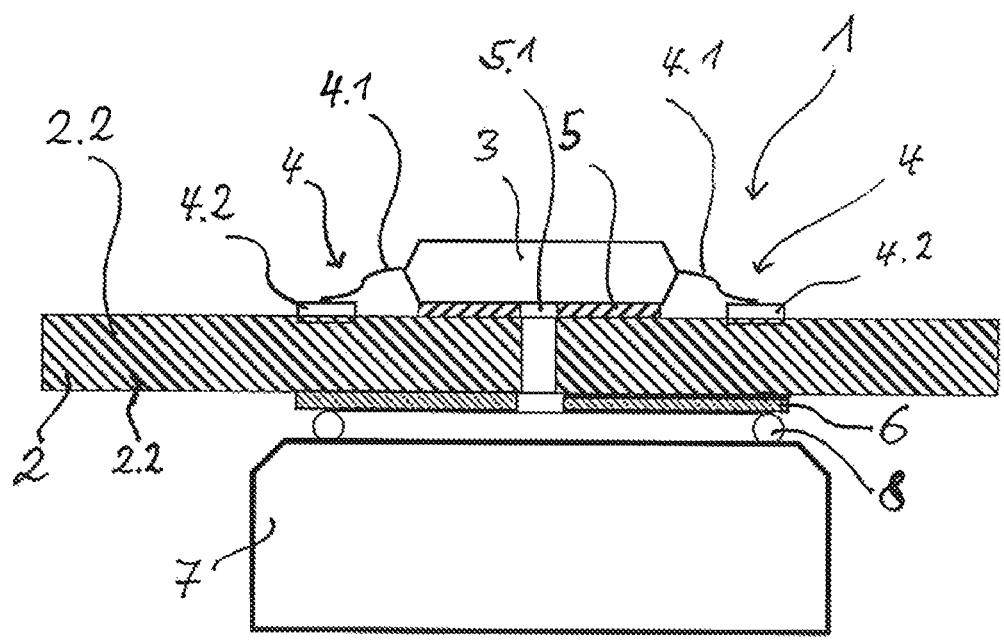
FIG. 2 shows a schematic illustration of the 2. connection unit.

FIG. 2 shows a connection unit with a pressure measuring unit 1 according to FIG. 1. A user hydraulic component 7 to be monitored is connected to the pressure measuring unit 1 by means of the hydraulic interface 6.

To this end, the user hydraulic component 7 is fastened to the hydraulic interface 6 in a pressure-tight manner such that an external pressure cannot act on the pressure sensor 3. For this purpose, the hydraulic interface 6 is connected to the user hydraulic component 7 in a gas- or liquid-tight manner with respect to its surroundings by means of an annular sealing part 8. An elastic O-ring is used for the seal 8.

The invention claimed is:

1. A pressure measuring unit for determining the oil pressure in a motor vehicle transmission, comprising a circuit carrier, a pressure sensor, an electrical interface, a mechanical interface and a hydraulic interface, wherein
the pressure sensor is electrically connected to the circuit carrier by the electrical interface and mechanically connected to the circuit carrier by the mechanical interface on the first side of the circuit carrier, wherein
the hydraulic interface configured to connect the pressure measuring unit to a user hydraulic component is arranged on a side of the circuit carrier that is situated opposite the first side, wherein
an opening is arranged in the circuit carrier for pressure equalization between the pressure sensor and the hydraulic interface,
an opening formed as part of the mechanical interface which is in fluid communication with the opening arranged in the circuit carrier;
wherein the pressure sensor is embodied as a surface mount device (SMD) component.

2. The pressure measuring unit as claimed in claim 1, wherein the electrical interface comprises an electrical connecting part of the pressure sensor and a contact area of the circuit carrier.

3. The pressure measuring unit as claimed in claim 1, wherein the mechanical interface is an adhesive bond.

4. The pressure measuring unit as claimed in claim 1, wherein the circuit carrier is a constituent part of a transmission control unit.

5. A connection unit comprising:
a pressure measuring, further comprising:
a circuit carrier, a pressure sensor, an electrical interface, a mechanical interface and a hydraulic interface, wherein
the pressure sensor is electrically connected to the circuit carrier by the electrical interface and mechanically connected to the circuit carrier by the mechanical interface on the first side of the circuit carrier, wherein
the hydraulic interface configured to connect the pressure measuring unit to a user hydraulic component is arranged on a side of the circuit carrier that is situated opposite the first side, wherein
an opening is arranged in the circuit carrier for pressure equalization between the pressure sensor and the hydraulic interface,
an opening formed as part of the mechanical interface which is in fluid communication with the opening arranged in the circuit carrier;
wherein the pressure sensor is embodied as a surface mount device (SMD) component;
wherein a user hydraulic component is connected to the pressure measuring unit by the hydraulic interface.

6. The connection unit as claimed in claim 5, wherein the hydraulic interface is connected to the user hydraulic component in a gas- or liquid-tight manner with respect to its surroundings by an annular sealing part.

7. The connection unit as claimed in claim 5, the electrical interface further comprising an electrical connecting part of the pressure sensor and a contact area of the circuit carrier.

8. The connection unit as claimed in claim 5, the mechanical interface further comprising an adhesive bond.

9. The connection unit as claimed in claim 5, wherein the circuit carrier is a constituent part of a transmission control unit.

* * * * *